United States Patent [19]

White

[11] Patent Number: 4,550,114

[45] Date of Patent: Oct. 29, 1985

[54] BENZOQUINOLIZINES AS α₂-ADRENOCEPTOR ANTAGONISTS

[75] Inventor: John F. White, Wokingham, England

[73] Assignee: John Wyeth & Brother limited, Maidenhead, England

[21] Appl. No.: 567,469

[22] Filed: Jan. 3, 1984

[30] Foreign Application Priority Data

Jan. 29, 1983 [GB] United Kingdom ............... 8302499

[51] Int. Cl.⁴ .................. A61K 31/47; C07D 455/06
[52] U.S. Cl. .................................. 514/294; 546/95; 546/96
[58] Field of Search ............... 546/95, 96; 424/258; 514/294

[56] References Cited

U.S. PATENT DOCUMENTS 4,076,820  2/1978  Archibald et al. ............... 424/258
4,183,937  1/1980  Ward .............................. 546/95 X

FOREIGN PATENT DOCUMENTS 2083029  8/1981  United Kingdom ............ 424/258

*Primary Examiner*—Richard A. Schwartz
*Attorney, Agent, or Firm*—George Tarnowski

[57] ABSTRACT

The invention concerns benzoquinolizines of general formula

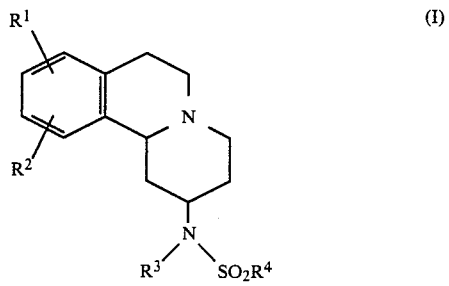

and their pharmaceutically acceptable acid addition salts. In the formula $R^1$ and $R^2$ which may be the same or different each represent hydrogen, lower alkyl, lower alkoxy or halogen, $R^3$ represents hydrogen or lower alkyl and $R^4$ represents a heterocyclic radical attached to the $SO_2$ group through a carbon atom of the heterocyclic ring. The compounds possess α₂-adrenoceptor antagonistic activity in warm blooded animals.

9 Claims, No Drawings

BENZOQUINOLIZINES AS α₂-ADRENOCEPTOR ANTAGONISTS

The invention relates to benzoquinolizines, to processes for preparing the benzoquinolizines and to pharmaceutical preparations containing them.

The present invention provides benzoquinolizines of the general formula (I)

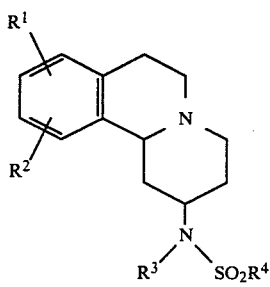

and the pharmaceutically acceptable acid addition salts thereof, wherein $R^1$ and $R^2$ which may be the same or different each represent hydrogen, lower alkyl, lower alkoxy or halogen, $R^3$ represents hydrogen or lower alkyl and $R^4$ represents a heterocyclic radical attached to the $SO_2$ group through a carbon atom of the heterocyclic ring.

The term "lower" as used herein means that the radical referred to contains 1 to 6 carbon atoms. Preferably the radical contains 1 to 4 carbon atoms.

Examples of $R^1$ and $R^2$ are hydrogen, lower alkyl such as methyl, ethyl, propyl or butyl, lower alkoxy such as methoxy, ethoxy, propoxy or butoxy or halogen such as chlorine, fluorine or bromine. $R^1$ and $R^2$ can be different or the same. Preferably, both $R^1$ and $R^2$ are hydrogen.

$R^3$ can be hydrogen or lower alkyl such as methyl, ethyl, propyl or butyl. Preferably $R^3$ is lower alkyl, particularly methyl.

The $R^4$ heterocyclic radical can be aromatic or nonaromatic. Preferably the heterocyclic radical is a mono or bicyclic heterocyclic group, which may be substituted or unsubstituted. The heterocyclic group may, for example, contain 1 or 2 hetero ring atoms, particularly nitrogen, oxygen or sulphur. Preferably the ring or each ring of the mono or bicyclic heterocyclic group contains 5 or 6 ring atoms (including the hetero atoms). The heterocyclic group may be substituted by one or more substituents. For example, the substituents may be selected from the group consisting of halogen (e.g. chlorine, fluorine or bromine), lower alkoxy (e.g. methoxy, ethoxy, propoxy or butoxy), lower alkyl (e.g. methyl, ethyl, propyl or butyl), alkylenedioxy (e.g. methylenedioxy or ethylenedioxy), amino, loweralkylamino, diloweralkylamino, trifluoromethyl, carbamoyl, phenyl and phenyl substituted by one or more of those substituents mentioned immediately above in connection with the heterocyclic group. Examples of heterocyclic radicals $R^4$ include substituted and unsubstituted quinoline, furan, thiophene, imidazole, pyridine, piperidine, pyrrolidine, indolyl and 1,2,3,4-tetrahydroquinoline.

The compounds of the invention can be prepared by a process in which an amine of general formula (II)

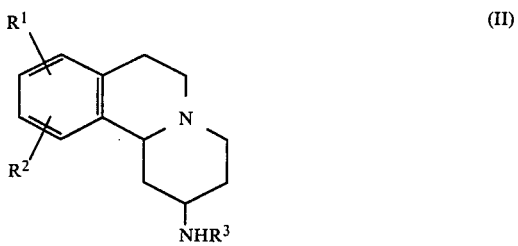

or an acid addition salt thereof (where $R^1$, $R^2$ and $R^3$ have the meanings given above) is reacted with a reactive derivative of a sulphonic acid compound of general formula (III)

$$R^4SO_2OH \qquad (III)$$

(where $R^4$ is as defined above) and, if required, converting a free base into a pharmaceutically acceptable acid addition salt. The reactive derivative of the sulphonic acid compound of general formula (III) can be, for example, the acid halide or anhydride. Preferably it is the halide, i.e. a compound of general formula $R^4SO_2X$ (where $R^4$ is as defined above and X is halogen, preferably chlorine). The reaction is preferably carried out under basic conditions, for example in the presence of a tertiary amine, e.g. triethylamine.

If in the process described above the compound of the invention is obtained as an acid addition salt, the free base can be obtained by basifying a solution of the acid addition salt. Conversely, if the product of the process is a free base, an acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The reactive derivatives of the sulphonic acid compound of general formula (III) are known compounds or they can be prepared by methods known in the art for preparing analogous compounds. Processes for preparing the amines of general formula (II) are described in UK Patent Specification 1,513,824.

The compounds of the invention possess two asymmetric carbon atoms and hence they can exist in various stereochemical forms. In addition they can exist as cis or trans isomers. It will be realised that if the starting material of formula (II) is a mixture of isomers the product of formula (I) will also be a mixture of isomers which can be separated, if required, by standard procedures. If the starting material is a single isomer then the product will also be a single isomer. Preferably the starting material of formula (II) is of the 2β-NHR³-1,3,4,6,7,11bα-hexahydroconfiguration.

The compounds of the invention possess pharmacological activity. For example the compounds are useful as antidepressants, in treatment of diabetes and in inhibiting blood platelet aggregation as evidenced by their α₂adrenoceptor antagonistic activity in warm blooded animals when tested by standard pharmacological test procedures.

The compounds of the invention were tested for $\alpha_2$adrenoceptor antagonistic activity on the rat field stimulated vas deferens preparation using a modification of the method of Drew, Eur. J. Pharmac., 1977, 42, 123–130. The procedure is described below.

Desheathed vas deferentia from sexually mature rats were suspended in a 6 ml organ bath in Krebs solution at 37° and bubbled with 5% $CO_2$ in oxygen. Platinum ring electrodes were positioned above and below the tissue for field stimulation, the stimulus parameters being 0.1 Hz 1 ms pulse width at supramaximal voltage. Twitch responses were recorded isotonically with 0.5 g loading. Clonidine hydrochloride was used as the $\alpha$-adrenoceptor agonist amd cumulative concentration-response curves were constructed for the inhibition of twitch obtained with clonidine in the range 0.125 to 4 ng ml$^{-1}$. After washing out clonidine, the twitch response quickly recovered and an antagonist was then introduced into the Krebs reservoir. Clonidine concentration-response curves were repeated 90 min after introduction of the antagonist. The concentration of clonidine producting 50% inhibition of twitch before and after introduction of antagonist were obtained and the dose-ratio for clonidine was calculated. Various concentrations of the antagonists were used.

These results were plotted in the manner described by Arunlakshana & Schild, Br. J. Pharmac. Chemother., 1959, 14, 48–58 and the values of pA$_2$ and slope were calculated. It was found, for example, that N-methyl-N-(1,3,4,6,7,11b$\alpha$-hexahydro-2H-benzo[a]-quinolizin-2$\beta$-yl)quinoline-8-sulphonamide and N-methyl-N-(1,3,4,6,7,11b$\alpha$-hexahydro-2H-benzo[a]-quinolizin-2$\beta$-yl)-3-pyridinesulphonamide, representative compounds of the invention, had pA$_2$ values of 8.46 and 8.22 respectively.

The compounds of the invention, in general, antagonise the $\alpha_2$-adrenoceptors to a greater extent than the $\alpha_1$-adrenoceptors. The $\alpha_1$ antagonistic activity can be evaluated by a method based on that of Gillespie, Br. J. Pharmac., 1972, 45, 404–416. In the procedure male rats (250–360 g) are killed by a blow on the head and bled. The two anococcygeus muscles are removed from their position in the pelvic cavity, where they arise from the upper coccygeal vertebrae. The muscles are suspended in 5 ml organ baths in Krebs solution containing 10$^{-4}$M ascorbic acid, to prevent drug oxidation. The tissues are gassed with a 95% oxygen, 5% $CO_2$ mixture and maintained at 37° C. Longitudinal muscle contractions are recorded using isotonic transducers. Cumulative dose response curves are then obtained to phenylephrine or in some cases methoxamine, both agents being presynaptic $\alpha_1$ alpha adrenoceptor agonists. The concentration range of phenylephrine or methoxamine used is 0.02 to 0.8 $\mu$g.ml$^{-1}$. The agonist is then washed from the bath and the test drug added to the bathing medium at a concentration of 10$^{-6}$M. After 30 min. equilibration with the test drug a further agonist dose response curve is obtained. The washing, equilibration and agonists dosing procedures are then repeated using 10$^{-5}$M and 10$^{-4}$M solutions of the test drug. Estimates of the pA$_2$ value for the test drug as an antagonist of phenylephrine or methoxamine were made from the agonist dose-ratios using the method of Arunlakshana & Schild, Br. J. Pharmac. Chemother., 1959, 14, 48–58. The pA$_2$ for $\alpha_1$ antagonistic activity and the $\alpha_2/\alpha_1$ selectivity ratio for N-methyl-N-(1,3,4,6,7,11b$\alpha$-hexahydro-2H-benzo[$\alpha$]quinolizin-2$\beta$-yl) quinoline-8-sulphonamide are respectively 6.84 and 42 and for N-methyl-N-(1,3,4,6,7,11b$\alpha$-hexahydro-2H-benzo[a]quinolizin-2$\beta$-yl)-3-pyridinesulphonamide are respectively 6.73 and 31.

Some of the compounds of the invention, for example, N-methyl-N-(1,3,4,6,7,11b$\alpha$-hexahydro-2H-benzo[a]quinolizin-2$\beta$-yl)-3-pyridinesulphonamide and N-(1,3,4,6, 7,11b$\alpha$-hexahydro-2H-benzo[a]quinolizin-2$\beta$-yl)pyridine-3-sulphonamide, also possess antihypertensive activity as determined by standard pharmacological test procedures in hypertensive rats.

The invention further provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

N-Methyl-N-(1,3,4,6,7,11bα-hexahydro-2H-benzo[a]-quinolizin-2β-yl)quinoline-8-sulphonamide An ice-cold stirred solution of 2β-methylamino-1,3,4,6,7,11bα-hexahydro-2H-benzo[a]quinolizine (2.16 g) and triethylamine (1.2 g) in dichloromethane (25 cm$^3$) was treated with a suspension of 8-quinolinesulphonyl chloride (2.28 g) in dichloromethane(25 cm$^3$). The clear solution was kept at room temperature for 8 days, washed with water and brine and dried (MgSO$_4$). Filtration and evaporation gave a yellow syrup which slowly crystallised from ethanol. The pale cream crystals were suspended in hot ethanol, acidified with ethanolic HCl and the clear solution cooled. The crystals which separated were triturated well with ethanol containing a little ethanolic HCl, collected by filtration and dried at 80°/100 mm to give the title compound as the monohydrochloride, hydrate (3.00 g), colourless crystals, m.p. 176°–181° (dec).

EXAMPLE 2

N-Methyl-N-(1,3,4,6,7,11bα-hexahydro-2H-benzo[a]-quinolizin-2β-yl)-2-carbamoylfuran-4-sulphonamide An ice-cold stirred solution of 2β-methylamino-1,3,4,6,7,11bα-hexahydro-2H-benzo[a]quinolizine (0.57 g) and triethylamine (0.4 g) in dichloromethane (15 cm$^3$) was stirred as a solution of 2-carboxamidofuran-4-sulphonyl chloride (0.55g containing a little of the 5-sulphonyl chloride) in dichloromethane (15 cm$^3$) was added slowly. The dark, clear solution was kept at room temperature for 3 days, washed with water (2×50 cm$^3$) and dried (MgSO$_4$). Filtration and evaporation gave a pink glass (0.87 g) which was chromatographed on silica eluted with 5–20% ethanol-toluene. The main fraction was a pale yellow solid (0.4 g) which was dissolved in ethanol, acidified with ethanolic HCl and cooled. The crystals which separated were triturated with boiling ethanol/water to give the title compound as the hydrochloride (0.30 g), as pale cream crystals, m.p. 258°–262° (dec), contaminated with a little of the 5-sulphonamide isomer.

EXAMPLE 3

N-Methyl-N-(1,3,4,6,7,11bα-hexahydro-2H-benzo[a]quinolizin-2β-yl)thiophene-2-sulphonamide An ice-cold, stirred solution of 2β-methylamino-1,3,4,6,7,11bα-hexahydro-2H-benzo[a]quinolizine (2.08 g) and triethylamine (1.2 g) in dichloromethane (25 cm$^3$) was treated with a solution of 2-thiophenesulphonyl chloride (1.76 g) in dichloromethane (25 cm$^3$). The clear solution was kept at room temperature for 4 days, washed with water and brine and dried (MgSO$_4$). Evaporation gave an orange syrup which was chromatographed on silica eluted with 10% ethanol-ethyl acetate to give a red-brown syrup (2.18 g) which was taken up in hot ethanol (10 cm$^3$), acidified with ethanolic HCl, diluted with ethyl acetate (25 cm$^3$) and cooled to give crystals which were collected by filtration, washed well with ethyl acetate and dried to give the title compound as the hydrochloride (1.60 g), pale buff crystals, m.p. 220°–3° (dec).

EXAMPLE 4

N-Methyl-N-(1,3,4,6,7,11bα-hexahydro-2H-benzo[a]-quinolizin-2β-yl)-2-(3,4-dichlorophenyl)imidazole-4-sulphonamide An ice-cold, stirred solution of 2β-methylamino-1,3,4,6,7,11bα-hexahydro-2H-benzo[a]quinolizine (2.16 g) and triethylamine (3 g) in dichloromethane (25 cm$^3$) was treated with crude 2-(3,4-dichlorophenyl)imidazole-4-sulphonyl chloride (4.4 g). The dark solution was kept at room temperature for 3 days, washed with water and brine and dried (MgSO$_4$). Evaporation gave a dark syrup which was chromatographed on silica eluted with 10% ethanol-ethyl acetate to give a yellow glass (1.69 g). This was dissolved in hot ethanol (10 cm$^3$), acidified with ethanolic HCl and cooled. The crystals which separated were collected by filtration, then triturated with boiling ethanol (15 cm$^3$) and water (3 cm$^3$) cooled and re-filtered to give the title compound as the hydrochloride (1.19 g), pale cream crystals, m.p. 245°–250° (decomp) (decomp. begins above 220°).

EXAMPLE 5

N-Methyl-N-(1,3,4,6,7,11bα-hexahydro-2H-benzo[a]-quinolizin-2β-yl)-3-pyridine sulphonamide (A) Preparation of Pyridine-3-Sulphonyl chloride A mixture of pyridine-3-sulphonic acid (3.0 g) and PCl$_5$ (7.9 g) was stirred in an oil bath maintained at 150° for 3 hours, in a flask fitted with a reflux condenser. After cooling, the liquid formed set solid. The solid was triturated with xylene (10 cm$^3$) and evaporated at the water pump in an oil-bath maintained at a maximum temperature of 110°, and with a splash-head to reduce frothing. The evaporation was repeated twice more, and the residue was pumped on a rotary evaporator to remove the last traces of xylene. The yellow, semi-crystalline mass (6.87 g) occluded unreacted PCl$_5$.

The crude product was used at once in the procedure of Example 5(B) below.

(B) Preparation of N-methyl-N-(1,3,4,6,7,11bα-hexahydro-2H-benzo[a]-quinolizin-2β-yl)-3-pyridinesulphonamide An ice-cold, stirred solution of 2β-methylamino-1,3,4,6,7,11bα-hexahydro-2H-benzo[a]quinolizine (1.80 g) and triethylamine (2.0 g) in dichloromethane (25 cm³) was treated with a suspension of crude pyridine-3-sulphonyl chloride (1.5 g) in dichloromethane (15 cm³). The clear solution was kept at room temperature for 6 days, washed with water (2×50 cm³) and dried (MgSO₄). Filtration and evaporation gave a dark red syrup (2.74 g) which was chromatographed on silica eluted with 10% ethanol-ethyl acetate to give a yellow syrup (1.61 g) which crystallised on standing. The solid was dissolved in hot ethanol (5 cm³), acidified with ethanolic HCl, diluted with ethyl acetate (10 cm³) and cooled. The sticky, pink crystals which separated were recrystallised from ethanol, filtered and dried to give the title product as the monohydrochloride, hemihydrate (1.01 g), pale pink, hygroscopic crystals, m.p. 155°–190° (dec).

EXAMPLE 6

N-(1,3,4,6,7,11bα-hexahydro-2H-benzo[a]quinolizin-2β-yl)pyridine-3-sulphonamide

An ice-cold, stirred solution of 2β-amino-1,3,4,6,7,11bα-hexahydro-2H-benzo[a]quinolizine (3.8 g) and triethylamine (2.5 g) in dichloromethane (50 cm³) was treated with a suspension of freshly-prepared pyridine-3-sulphonyl chloride (0.0188M) in dichloromethane (25 cm³). The mixture was stirred at room temperature for 2 hours, then the clear solution kept for 2 days. It was then washed with water and brine, and dried (MgSO⁴). Filtration and evaporation gave a dark syrup (3.47 g) which was chromatographed on silica eluted with 10% ethanol-ethyl acetate, to give a yellow solid (2.37 g). This was triturated with boiling ethanol (10 cm³), cooled in ice and filtered to give the title compound as colourless crystals.

The base was taken up in boiling ethanol, strongly acidified with ethanolic HCl, diluted with ethyl acetate and cooled. Crystals formed from the clear solution over 2–3 days; these were filtered off and washed well to give the title compound as the hydrochloride (1.32 g) colourless crystals, m.p. 225°–231° (dec).

I claim:

1. A compound selected from the group consisting of a benzoquinolizine of the formula

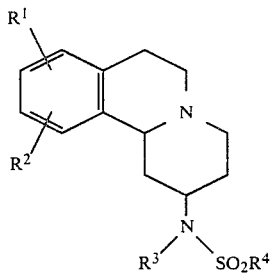

and a pharmaceutically acceptable acid addition salt thereof, wherein R¹ and R² which may be the same or different each represent hydrogen, lower alkyl, lower alkoxy or halogen, R³ represents hydrogen or lower alkyl and R⁴ represents a heterocyclic radical attached to the SO₂ group through a carbon atom of the heterocyclic ring selected from the group consisting of substituted or unsubstituted quinoline, furan, thiophene, pyridine, imidazole, indolyl or 1,2,3,4-tetrahydroquinoline, and said substituents are selected from the group consisting of halogen, lower alkoxy, lower alkyl, lower alkylenedioxy, amino, lower alkylamino, diloweralkylamino, trifluoromethyl, carbamoyl, phenyl or phenyl substituted by one or more of the R⁴ heterocyclic radical substituents.

2. A compound according to claim 1 which is N-methyl-N-(1,3,4,6,7,11bα-hexahydro-2H-benzo[a]quinolizin-2β-yl)quinoline-8-sulphonamide or a pharmaceutically acceptable acid addition salt thereof.

3. A compound according to claim 1 which is N-methyl-N-(1,3,4,6,7,11bα-hexahydro-2H-benzo[a]quinolizin-2β-yl)-2-carbamoylfuran-4-sulphonamide or a pharmaceutically acceptable acid addition salt thereof.

4. A compound according to claim 1 which is N-methyl-N-(1,3,4,6,7,11bα-hexahydro-2H-benzo[a]quinolizin-2β-yl) thiophene-2-sulphonamide or a pharmaceutically acceptable acid addition salt thereof.

5. A compound according to claim 1 which is N-methyl-N-(1,3,4,6,7,11bα-hexahydro-2H-benzo[a]quinolizin-2β-yl)-3-pyridine sulphonamide or a pharmaceutically acceptable acid addition salt thereof.

6. A compound according to claim 1 which is N-(1,3,4,6,7, 11bα-hexahydro-2H-benzo[a]quinolizin-2β-yl)pyridine-3-sulphonamide or a pharmaceutically acceptable acid addition salt thereof.

7. A compound according to claim 1 which is N-methyl-N-1,3,4,6,7,11bα-hexahydro-2H-benzo[a]quinolizin-2β-yl)-2-(3,4-dichlorophenyl)imidazole-4-sulphonamide or a pharmaceutically acceptable acid addition salt thereof.

8. A pharmaceutical composition having $\alpha_2$-adrenoceptor antagonistic activity comprising an amount effective to antagonise $\alpha_2$-adrenoceptors of a compound selected from the group consisting of a benzoquinolizine of the formula

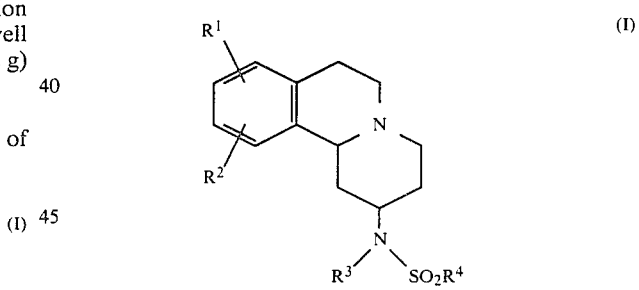

and a pharmaceutically acceptable acid addition salt thereof, wherein R¹ and R² which may be the same or different each represent hydrogen, lower alkyl, lower alkoxy or halogen, R³ represents hydrogen or lower alkyl and R⁴ represents a heterocyclic radical attached to the SO₂ group through a carbon atom of the heterocyclic ring selected from the group consisting of substituted or unsubstituted quinoline, furan, thiophene, pyridine, imidazole, indolyl or 1,2,3,4-tetrahydroquinoline, and said substituents are selected from the group consisting of halogen, lower alkoxy, lower alkyl, lower alkylenedioxy, amino, lower alkylamino, diloweralkylamino, trifluoromethyl, carbamoyl, phenyl or phenyl substituted by one or more of the R⁴ heterocyclic radical substituents, in association with a pharmaceutically acceptable carrier.

9. A method of selectively antagonising $\alpha_2$-adrenoceptors in warm blooded animals which comprises administering to the animal an effective amount of a compound selected from the group consisting of a benzoquinolizine of the formula

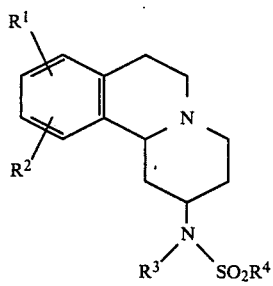

(I)

and a pharmaceutically acceptable acid addition salt thereof, wherein $R^1$ and $R^2$ which may be the same or different each represent hydrogen, lower alkyl, lower alkoxy or halogen, $R^3$ represents hydrogen or lower alkyl and $R^4$ represents a heterocyclic radical attached to the $SO_2$ group through a carbon atom of the heterocyclic ring selected from the group consisting of substituted or unsubstituted quinoline, furan, thiophene, pyridine, imidazole, indolyl or 1,2,3,4-tetrahydroquinoline, and said substituents are selected from the group consisting of halogen, lower alkoxy, lower alkyl, lower alkylenedioxy, amino, lower alkylamino, diloweralkylamino, trifluoromethyl, carbamoyl, phenyl or phenyl substituted by one or more of the $R^4$ heterocyclic radical substituents.

* * * * *